United States Patent [19]

Maine et al.

[11] Patent Number: 5,024,941
[45] Date of Patent: Jun. 18, 1991

[54] EXPRESSION AND SECRETION VECTOR FOR YEAST CONTAINING A GLUCOAMYLASE SIGNAL SEQUENCE

[75] Inventors: Gregory T. Maine, Watertown; Robert S. Daves, Reading; Robert R. Yocum, Arlington, all of Mass.

[73] Assignee: BioTechnica International, Inc., Cambridge, Mass.

[21] Appl. No.: 810,423

[22] Filed: Dec. 18, 1985

[51] Int. Cl.$^5$ .................. C12P 21/00; C12N 15/00; C12N 5/03
[52] U.S. Cl. .................. 435/69.9; 435/691; 435/698; 435/202; 435/203; 435/204; 435/205; 435/255; 435/256; 435/320.1; 536/27; 935/47; 935/48
[58] Field of Search .................. 435/172.1, 172.3, 202, 435/203, 204, 205, 940, 942; 935/60, 28, 69

[56] References Cited

U.S. PATENT DOCUMENTS

| | | | |
|---|---|---|---|
| 4,546,082 | 10/1985 | Kurjan | 435/172.3 |
| 4,727,028 | 2/1988 | Santerre et al. | 435/240.2 |

FOREIGN PATENT DOCUMENTS

| | | | |
|---|---|---|---|
| 0088632 | 9/1983 | European Pat. Off. | 435/69.1 |
| 0123294 | 10/1984 | European Pat. Off. | 435/69.1 |
| 0123544 | 10/1984 | European Pat. Off. | 435/69.1 |
| 0127304 | 12/1987 | European Pat. Off. | |
| 0116201 | 8/1989 | European Pat. Off. | 435/69.1 |
| 0121884 | 10/1989 | European Pat. Off. | 435/69.1 |
| 8401153 | 3/1984 | PCT Int'l Appl. | |

OTHER PUBLICATIONS

Smith, R. A. et al.; Heterologous Protein Secretion from Yeast; Science 229, pp. 1219–1223 (1985).
Innis, M. A. et al.; Expression, Glycosylation and Secretion of an Aspergillus Glucoamylase by Saccharomyces Cerevisiae, Science, 228, pp. 21–26 (1985).
Yamashita, I., and S. Fukui; Secretion of S. Diastatrus Glucoamylase from S. Ponbe; Agric. Biol. Chem 48, pp. 1931–1932 (1984).
Meaden, P. et al.; A Dex Gene Conferring Production of Extracellular Amyloglucosidase on Yeast; Gene 34, pp. 325–334 (1985).
Yamashita, I. et al.; Cloning and Expression of the S. fiyuligera glucoamylase gene in S. cerevisiae, Appl. Microbiol Biotechnol 23; pp. 130–133 (1985).
PCT; Nunberg, J. H. et al.; Glucoamylase cDNA; Aug. 2, 1984.
Yamashita, I. and S. Fukui; Molecular Cloning of a Glucoamylase-Producing Gene in the Yeast Succharomyces; Agric. Biol. Chem. 47, pp. 2689–2692.
Yamashita, I. et al.; Nucleotide Sequence of the Extracellular Glycoamylase Gene STA1 in the yeast S. Diastaticus; J. Bacteriol 161, pp. 567–573 (1985).
Yamashita, I. et al.; Polymorphic Extracellular Glycoamylase Genes and Their Evolutionary Origin in the Yeast S. Diastaticus; J. Bacteriol. 161, pp. 574–582 (1985).
Brown et al., (1984), M.G.G. 197:351.
Smith et al. (1985) Science, 229: 1219.
Taussig et al. (1983), Nucl. Acid Res. 11:1943.

Primary Examiner—Robin L. Teskin
Attorney, Agent, or Firm—Fish & Richardson

[57] ABSTRACT

A vector including a DNA sequence encoding a secretory signal sequence substantially identical to the secretory signal-encoding sequence of a glucoamylase gene from *Saccharomyces diastaticus* or *S. cerevisiae;* and upstream from the signal-encoding sequence, a DNA sequence capable of promoting transcription in yeast (e.g., a high yield promoter, such as the promoter of the triose phosphate isomerase gene), transcription of the signal-encoding sequence being under the control of the transcription-promoting sequence, a site for the insertion into the vector of a heterologous DNA sequence, in reading frame with the signal-encoding sequence. The vector is useful as an expression vector in yeast.

10 Claims, 8 Drawing Sheets

```
       -260                      -250                      -240                      -230                      -220                      -210
        *                         *                         *                         *                         *                         *
A      ATC   GGG   CCA   GAG   TAA   CAC   CCA   ATA   GCA   CTC   GTA   CAA   GGT   GCT   TTA   ACT   TGC   CTG   CAT

-200                      -190                      -180                      -170                      -160                      -150
        *                         *                         *                         *                         *                         *
       GTG   TGG   ACT   CAC   AAA   TTA   GGG   GAC   TCA   GGC   ACA   GAA   GCA   AGG   GTC   CTT   TTC   GGT   TCC   CTG

-140                      -130                      -120                      -110                      -100                       -90
        *                         *                         *                         *                         *                         *
       TTT   CCT   CCT   GCG   CAT   TTC   GTA   TTT   CTC   TGG   TCT   TGG   CTC   ATC   TGG   CGT   TAT   CTG   TTC

-80                       -70                       -60                       -50                       -40                       -30
         *                         *                         *                         *                         *                         *
       TGT   TAC   ACA   AGA   AAT   CGT   ACA   TTT   ACA   ATA   TAG   TGA   TAA   TCG   TGG   ACT   AGA   GCA   AGA   TTT
```

```
-20
 *
CAA ATA AGT AAC AGC AAA AGC

-10
                               *
                              AAC 40                                        1
  *                                        *
 ATG CTC AGC GTA GGA TTC GGG              ATG GCA AGA CAA AAG ATG
 Met Leu Ser Val Gly Phe Gly              Met Ala Arg Gln Lys Met 10                    20                    30
                                   *                     *                     *
                                  CAA AAG ATG           TTT TAT AAC           AAA TTA CTC GGC
                                  Gln Lys Met           Phe Tyr Asn           Lys Leu Leu Gly

100
  *
 GAC TTT GGC AAG GGC ATT CTC              GAT CAA GCT TGG TGG CTC GAG
 Asp Phe Gly Lys Gly Ile Leu              Asp Gln Ala Trp Trp Leu Glu 70                    80                    90
                                   *                     *                     *
                                  GCG GCT GCT           AAC ATT ACT           ATA TAC GAA TTT
                                  Ala Ala Ala           Asn Ile Thr           Ile Tyr Glu Phe

160
 TCG CAA GTG CAG CTG CGG AGT AGT          GCA GTC TTG ATG AAT GGG
 Ser Gln Val Gln Leu Arg Ser Ser          Ala Val Leu Met Asn Gly 130                   140                   150
                                  TAC GGC TAC           TTT TCA              AAC AAC GGC TCT
                                  Tyr Gly Tyr           Phe Ser              Asn Asn Gly Ser

220
  *
 GGC GCT TGG CAC AGT AGT AGT CTC CAG GAG ATG AAT CTG CTG TTG
 Gly Ala Trp His Ser Ser Ser Leu Gln Glu Met Asn Leu Leu Leu 190                   200                   210
                                   *                     *                     *
                                  ATG AAT GGG           ACA CTG GTA           TAC TAT GAT TCA AAC
                                  Met Asn Gly           Thr Val Val           Tyr Tyr Asp Ser Asn

280
  *
 GAA AAA ATA TTT GAA AAT ATT GGG CCC AGC GCC CTG TAT CCG TCT
 Glu Lys Ile Phe Glu Asn Ile Gly Pro Ser Ala Leu Tyr Pro Ser 250                   260                   270
                                   *                     *                     *
                                  TGG CTC CAG           GGA CAG AAA           AAA GTT TCC ATC
                                  Trp Leu Gln           Gly Gln Lys           Lys Val Ser Ile 310                   320                   330
                                   *                     *                     *
                                  GCC CTG TAT           CCG TCT ATT           TCG CCT GGG CTC GTC
                                  Ala Leu Tyr           Pro Ser Ile           Ser Pro Gly Val
```

*(Figure reproduced from patent — sequence layout approximate; see original for definitive reading.)*

```
340  CTG ATT GCG TCA CCA TCG CAA ACG CAT CCA GAC TAC TTC TAC CAA TGG ATA AGG CAC AGC
     Val Ile Ala Ser Pro Ser Gln Thr His Pro Asp Tyr Phe Tyr Gln Trp Ile Arg Asp Ser
                     350*        360*            370*        380*        390*

400  GCG TTG ACG ATA AAC AGT ATT GTC TCT CAT TCT GCG GGC CCG GCA ATA GAG ACG TTA TTG
     Ala Leu Thr Ile Asn Ser Ile Val Ser His Ser Ala Gly Pro Ala Ile Glu Thr Leu Leu
                     410*        420*            430*        440*        450*

460  CAG TAC CTG AAC GTT TCA TTC CAC TTG CAA AGA AGC AAC AAC ACA TTG GGC GCT GGC ATT
     Gln Tyr Leu Asn Val Ser Phe His Leu Gln Arg Ser Asn Asn Thr Leu Gly Ala Gly Ile
                     470*        480*            490*        500*        510*

520  GGT TAC ACT AAC GAT ACA GTG GCT TTG GGA GAC CCT AAG TGG AAC GTC GAC GGC ACG GCT
     Gly Tyr Thr Asn Asp Thr Val Ala Leu Gly Asp Pro Lys Trp Asn Val Asp Gly Thr Ala
                     530*        540*            550*        560*        570*

580  TTC ACG GAA GAT TGG GGT CGT CCT CAA AAC GAT GGG CCT GCT CTT CGA AGC ATT GCC ATC
     Phe Thr Glu Asp Trp Gly Arg Pro Gln Asn Asp Gly Pro Ala Leu Arg Ser Ile Ala Ile
                     590*        600*            610*        620*        630*

640  TTA AAA ATC ATC GAT GAT ATC AAG CAA TCT GGC ACT GAT CTG GGG GCC AAG TAC CCA TTC
     Lue Lys Ile Ile Asp Asp Ile Lys Gln Ser Gly Thr Asp Leu Gly Ala Lys Tyr Pro Phe
                     650*        660*            670*        680*        690*
```

FIG. 3-3

| 700 * | | 710 * | | | 720 * | | | 730 * | | | 740 * | | | 750 * | | | |
|---|---|---|---|---|---|---|---|---|---|---|---|---|---|---|---|---|---|
| CAG | TCC | GCA | GAT | ATC | TTT | GAT | ATT | GTA | CGT | TGG | GAC | CTG | AGG | TTC | ATT | ATT | GAC |
| Gln | Ser | Ala | Asp | Ile | Phe | Asp | Ile | Val | Arg | Trp | Asp | Leu | Arg | Phe | Ile | Ile | Asp |

| 760 * | | 770 * | | | 780 * | | | 790 * | | | 800 * | | | 810 * | | | |
|---|---|---|---|---|---|---|---|---|---|---|---|---|---|---|---|---|---|
| CAC | TGG | AAT | TCT | TCC | TTT | GAT | CTA | GAG | GAA | TGG | AAT | GGC | ATG | CAT | TTC | TTT | ACT |
| His | Trp | Asn | Ser | Gly | Phe | Asp | Leu | Glu | Glu | Trp | Asn | Gly | Met | His | Phe | Phe | Thr |

| 820 * | | 830 * | | | 840 * | | | 850 * | | | 860 * | | | 870 * | | | |
|---|---|---|---|---|---|---|---|---|---|---|---|---|---|---|---|---|---|
| TTA | CTG | GTA | CAA | CTG | TCT | GCA | GTG | GAC | AAC | CTG | TCG | TAT | TTT | AAC | GCC | TCA | GAA | CGG |
| Leu | Leu | Val | Gln | Leu | Ser | Ala | Val | Asp | Lys | Leu | Ser | Tyr | Phe | Asn | Ala | Ser | Glu | Arg |

LeuGluAsnIleThrSerAspArgProLeu

5'- TCGAGAACATTACTAGCGATAGACCTTTG
    CTTGTAATGATCGCTATCTGGAAACCAG-5'

DEX4 ←⊨→ SUC2

EXPRESSION AND SECRETION VECTOR FOR YEAST CONTAINING A GLUCOAMYLASE SIGNAL SEQUENCE

BACKGROUND OF THE INVENTION

This invention relates to genetic engineering in yeast.

In the commercial production of proteins via recombinant DNA technologies, it is often advantageous for the desired protein to be secreted into the growth medium, in order to facilitate the recovery of the desired protein. Secretion of proteins from cells is generally accomplished by the presence of a short stretch of hydrophobic amino acids constituting the amino-terminal end of the primary translation product. This hydrophobic stretch is called the "secretory signal sequence", and it is possible to use such signal sequences to effect the secretion of heterologous proteins. This is generally accomplished by the construction of an expression vector comprising a DNA sequence encoding a secretory signal sequence, into which a gene encoding the desired heterologous protein is inserted. When such a plasmid is transformed into a host cell, the host cell will express the desired protein product and secrete the protein into the growth medium. Such secretion vectors have been constructed for a variety of microorganisms, including *E. coli* (Gilbert et al., U.S. Pat. No. 4,338,397) *B. subtilis, S. lividans* and *S. cerevisiae.*

Because of the considerable amount that is known about the genetics and molecular biology of *S. cerevisiae*, yeast is a desirable organism to use for secretion systems. Kurjan et al. (U.S. Pat. No. 4,546,082) discloses a yeast secretion vector based on the signal sequence from the alpha-factor gene.

SUMMARY OF THE INVENTION

In general, the invention features a vector including a DNA sequence encoding a secretory signal sequence of a glucoamylase gene from *Saccharomyces diastaticus* or *S. cerevisiae;* upstream from the signal-encoding sequence, a DNA sequence capable of promoting transcription in yeast, transcription of the signal-encoding sequence being under the control of the transcription-promoting sequence; and downstream from the signal-encoding sequence, a site for the insertion into the vector of a heterologous DNA sequence, in reading frame with the signal-encoding sequence.

In preferred embodiments, there is inserted at the insertion site, a heterologous gene, e.g., the *Aspergillus niger* glucoamylase gene, transcription of the heterologous gene being under the control of the transcription-promoting sequence controlling transcription of the secretory signal-encoding sequence; preferred such sequences are the promoter or upstream activation sequences of the *TPI* or *GAL1* genes of *S. cerevisiae.*

A desired protein can be produced by inserting a gene encoding the protein into the above vector at the site for insertion; transforming the vector into a yeast cell; culturing the yeast cell; and recovering the protein from the growth media.

In another aspect, the invention features a method for screening yeast cells for glucoamylase production, involving plating the cells on a solid support coated with a solid nutrient medium containing starch to which a visible dye is covalently coupled, culturing cells until colonies have grown, contacting the cells and support with a water-miscible organic solvent, and detecting halo formation on the support as an indication of glucoamylase production.

The organic solvent preferably is an alcohol such as ethanol, methanol, isopropanol or isoamyl alcohol, or one of DMSO, acetic acid, or acetone, and is most preferably 50–100%, v/v, ethanol. Other organic solvents can be screened for useful such solvents by testing the solvent in the above method, using a yeast strain known to secrete glucoamylase.

The above method takes advantage of our discovery that, although haloes produced by the action of secreted glucoamylase on dye-coupled starch are not easily visible directly following colony growth, they can be made visible by contacting the colonies and solid support with a polar solvent such as ethanol. The solvent diffuses into the medium and interacts with the products of digestion of the dye-coupled starch in a way (probably involving a precipitation reaction) which changes the visual characteristics of those products; the haloes, while not becoming clear in the process, are made to appear texturally distinct from undigested material, rendering them easily observable.

Yeast cells present certain advantages as a host for the production of commercially important protein molecules. Because yeast cells have been commercially fermented for centuries, it is advantageous to make use of this experience to ferment yeast cells that have been genetically engineered to synthesize desired proteins.

Saccharomyces species, e.g., *S. cerevisiae*, contain only one plasma membrane, so that some proteins are secreted into the culture medium. In contrast, *E. coli* cells have two membranes, the "inner" and "outer" membranes, so that proteins in these cells are usually secreted to the periplasmic space between the two membranes. *S. cerevisiae* is known to secrete a relatively small number of proteins (10–20) into the culture medium, making purification of secreted heterologous proteins relatively easy compared to purification of cytoplasmic proteins. In addition, S. cerevisiae produces relatively low levels of extracellular proteases, unlike *B. subtilis.* Finally, *S. cerevisiae* grows well on inexpensive media.

Generally, secretion into the medium is desirable in that it greatly simplifies purification of the desired polypeptide (from which the secretory signal is cleaved during secretion). Secretion also enhances the correct formation of disulfide bonds, which are essential for the biological activity of many proteins.

The signal sequence from the *S. diastaticus* DEX4 glucoamylase gene is a particularly advantageous choice in that it directs secretion of a bona fide protein rather than a small peptide, such as α-factor; and it directs secretion into the supernatant of yeast cultures, as opposed to the periplasmic space, where such proteins as invertase and phosphatase are found. The DEX4 signal has been shown to function properly in "unnatural" contexts, constructed in vitro. Thus it is expected that the DEX4 signal sequence will be useful to direct the secretion of other heterologous proteins from yeast cells.

One heterologous protein whose expression and secretion can be widely useful is the enzyme glucoamylase from *A. niger.* This enzyme has a number of commercial uses, including applications in brewing, corn syrup production and grain fermentation for distilled ethanol production.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagram of a plasmid of the invention, pRD112, and an outline of its construction. Abbreviations of restriction enzyme sites are as follows: A, XbaI; B, BamHI; BII, BssHII; E, EcoRI; H, HindIII; K, KpnI; M, SmaI; PII, PvuII; X, XhoI; S, SalI. The rectangular boxes show some of the protein coding regions. The inner concentric circle indicates the source of DNA for each part of the plasmid. Note that pRY271 contains two deletions internal to two of the DNA segments, a 275 base pair BamHI to SalI deletion in the pBR322 derived portion, and a 300 base pair deletion in the TPI gene that was created by digestion with BAL31 exonuclease followed by insertion of an EcoRI linker (5'-AGAATTCT). (E) represents a former EcoRI site that was destroyed during plasmid construction.

FIG. 2 shows restriction maps of the S. diastaticus DNA inserts in pGM11 and pGM13. Abbreviations are the same as in FIG. 1 with the following additional abbreviations: C, ClaI; G, BglII; Hp, HpaI; P, PstI; PI, PvuI; N, NcoI; V, EcoRV. Restriction maps to the right of the vertical arrows are identical and to the left of the arrows are different. The boxes indicate long open reading frames presumably coding for glucoamylases.

FIG. 3 shows the DNA sequence of the DEX4 gene from just upstream of the BamHI site to just downstream of the PstI site. Homology of approximately 98% between DEX4 and STA1 (DEX2) begins at base +97. No significant homology exists upstream from +97.

FIG. 4 shows the DNA sequence of the portion of pRD112 that covers the 5' end of the TPI-DEX4-A. niger glucoamylase gene fusion, including the synthetic adapter sequences. Bases −22 through +9 are derived from TPI. Bases +10 through +73 consist of a synthetic sequence based on the DEX4 protein's signal sequence. Note a change from the DEX4 DNA sequence that leaves the signal amino acid unaltered: a HindIII site has been introduced at bases +28 to +33. Bases +74 through +87 are derived from a synthetic XhoI to BssHII adapter, and bases +88 onward are derived from an A. niger glucoamylase cDNA clone, as described in more detail below.

FIG. 8 is the nucleotide sequence of a 58-base sequence used for construction of pRD105;

VECTOR COMPONENTS

Figure 1:
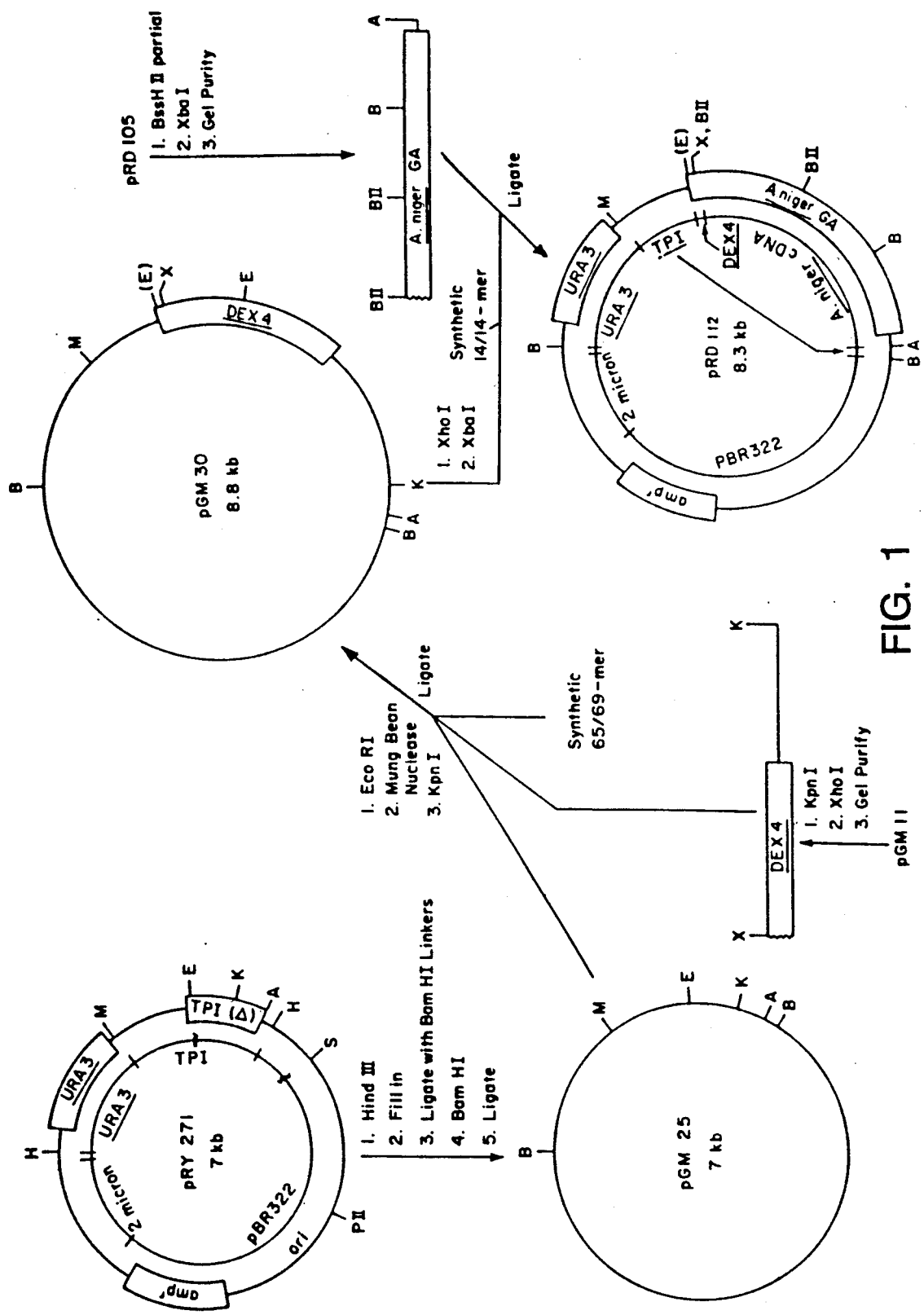

As is mentioned above, a vector of the invention useful for the transformation of host yeast cells for the production and secretion of a desired heterologous polypeptide includes several components, now discussed in more detail.

Transcription Promoting Sequences

Any sequences which function to promote transcription of genes in yeast can be employed. Preferably, these sequences are substantially identical to naturally occurring yeast promoters and yeast upstream activator sequences. The transcription-promoting sequences are preferably located upstream of the DNA encoding the in-frame secretory signal and heterologous protein-encoding sequences, and are preferably at a distance from the translational start site of the signal-encoding sequence which effects optimal expression. Suitable naturally occurring yeast sequences that promote transcription can be derived from the following genes: GAL1, GAL7, GAL10, ADH1, ADH2, PGK, PYK, GLD, ENO, TPI, DEX1 (STA2), DEX2 (STA1), Mα or any of the ribosomal RNA cistrons (see D. Fraenkel (1982) Carbohydrate Metabolism, in *The Molecular Biology of the Yeast Saccharomyces*, J. Strathern, E. Jones, and J. Broach, eds., Cold Spring Harbor Laboratory Press, Cold Spring Harbor, N.Y., pp 1–37).

S diastaticus Glucoamylase Secretory Signal Sequences

The DNA encoding the secretory signal sequence is preferably isolated from an S. diastaticus glucoamylase gene, or from a homologous S. cerevisiae gene, as described in more detail below. S. diastaticus is known to have several genes encoding secreted glucoamylase enzymes, including one which is expressed during vegetative growth (DEX1), and one which is generally expressed only during sporulation (DEX4). S. cerevisiae has a sporulation-specific glucoamylase gene that is homologous to DEX4. All of these genes are suitable sources for the isolation of a secretory signal sequence.

Alternatively, the DNA encoding the sequence can be produced synthetically using conventional DNA synthetic techniques. In addition, the DNA sequence (whether natural or synthetic) can be modified in any way which does not substantially impair the ability of the encoded signal sequence to effect secretion of the heterologous polypeptide.

The signal sequence and heterologous polypeptide together constitute a hybrid protein which, by virtue of the signal sequence, is transported through the membrane of the endoplasmic reticulum and out of the host yeast cell. In the course of secretion, the signal sequence (and "pro" sequence, if present; see below) are cleaved. Few or no extraneous amino acids will remain after cleavage of the signal sequence and, if present, "pro" sequence.

Terminator Sequences

Sequences which function as transcription terminators are thought to be necessary for optimal gene expression in eukaryotes such as yeast. Terminator sequences are located downstream from the site for insertion of the heterologous DNA sequence. Suitable terminator sequences can be derived from any gene listed above under "Transcription Promoting Sequences".

Heterologous DNA Sequence and Site

The site for insertion of the heterologous DNA sequence is downstream from the 3' end of the DNA encoding the signal sequence. This site may either be directly adjacent to the 3' end of the signal sequence or after an additional sequence found in some genes (i.e. a "pro" sequence) that may aid in the secretion process.

Insertion of the heterologous DNA sequence is facilitated if the restriction site is unique in the vector. The site can be naturally occurring in the vector, or it can be synthetically added.

Rather than inserting the heterologous gene into the vector adjacent to the signal-encoding or "pro" sequences, it can be advantageous in some instances (particularly in the case of small peptides and polypeptides) to introduce the heterologous gene into the vector in such a way as to produce a hybrid polypeptide, composed of all or a portion of the glucoamylase enzyme fused to the polypeptide encoded by the heterologous gene. The hybrid is more resistant to proteolysis than the desired polypeptide alone, and yield is thus increased. Following recovery of the hybrid polypeptide, the glucoamylase portion is removed, using conventional techniques.

The heterologous DNA can encode any desired polypeptide, e.g., medically useful proteins such as hormones, vaccines, antiviral proteins, antitumor proteins, antibodies, or blood clotting proteins, and agriculturally and industrially useful proteins such as enzymes or pesticides.

Figures 5, 6:
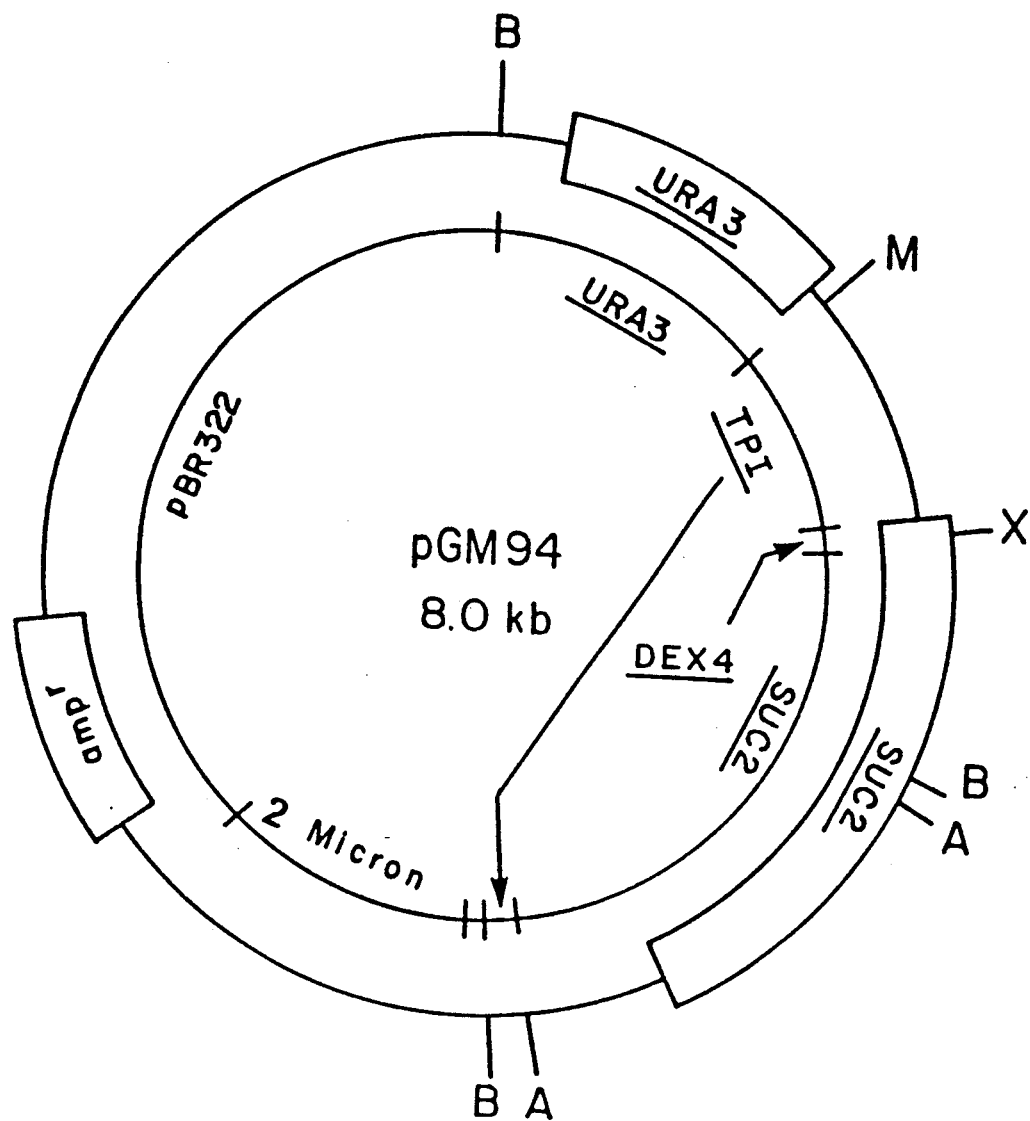
FIG. 5 shows the structure of pGM94, another vector of the invention, containing a TPI-DEX4-SUC2 fusion. Abbreviations are the same as in FIGS. 1 and 2.
FIG. 6 shows the DNA sequence, and corresponding protein sequence, of a synthetic 29/28-mer XhoI to AvaII adapter that was used to construct the TPI-DEX4-SUC2 fusion on pGM94.

The construction of two particular vectors of the invention, pRD112 and pGM94, is illustrated in FIG. 1 and FIG. 5, and described below.

Structure of Vectors

FIG. 1 contains a diagrammatic representation of the structure and construction of pRD112, a secretion vector capable of replication in *E. coli* and in *S. cerevisiae* in which the heterologous *A. niger* gene for the enzyme glucoamylase is inserted adjacent to the DNA encoding the DEX4 *S. diastaticus* glucoamylase signal sequence, under the transcriptional control of the triose phosphate isomerase (TPI) promoter from *S. cerevisiae*.

FIG. 5 contains a diagrammatic representation of pGM94, a secretion vector capable of replication in *E. coli* and in *S. cerevisiae* in which the *S. cerevisiae* SUC2 gene encoding invertase is inserted adjacent to the DNA encoding the DEX4 *S. diastaticus* glucoamylase signal sequence, under the transcriptional control of the triose phosphate isomerase (TPI) promoter from *S. cerevisiae*.

Construction of Vectors

The first step in the construction of pRD112 and pGM94 was the isolation of the *S. diastaticus* glucoamylase genes and their signal sequences, which was carried out as follows.

Isolation of S. diastaticus Glucoamylase Genes

A genomic DNA library of *S. diastaticus* strain 1354 (a DEX1), obtained from G. Stewart (Labatts Brewing Co.), was prepared in an *S. cerevisiae* - *E. coli* shuttle vector that contained the origin of replication from the yeast 2 micron circle and the URA3 gene for selection of transformants in ura3− yeasts (for example see Carlson and Botstein (1982) Cell 28: 145-154). Total *S. diastaticus* DNA was partially digested with Sau3AI, and DNA fragments between 5 and 10 kilobases were isolated on a sucrose gradient. This DNA was then ligated into the vector and transformed into *E. coli*. The bank contained about 40,000 independent clones with *S. diastaticus* inserts ranging from 5 to 10 kilobases.

The *S. diastaticus* library was introduced into *S. cerevisiae* strain RD61-1D (a leu2 his1 ura3 hom3 ade2 inh dex1°), and approximately 100,000 URA+ transformants were selected, pooled and plated on starch-azure plates at about 200 colonies per 100 mm petri plate. Starch azure (H. Rinderknecht et al. (1967) Experimentia 23: 805) plates contained 20 ml of bottom agar consisting of 20 g agar, 7 g Difco yeast nitrogen base, 0.7 g uracil dropout mix (Sherman, F., Hicks, J., and Fink, G.(1981) Methods in Yeast Genetics, Cold Spring Harbor Laboratory Press, Cold Spring Harbor, N.Y.), 30 g glycerol, and 20 g ethanol per liter and 10 ml of a top agar consisting of bottom agar plus 0.5% starch azure (Sigma). The top agar was mixed carefully just before pipetting it onto solidified bottom agar to ensure lack of bubbles and even distribution of the starch azure granules.

After colonies had grown to a diameter of 2-3 mm (usually 4-7 days), replicas of each plate were made on plates containing bottom agar plus 2% glucose. The starch azure master plates were then flooded with 10 ml ethanol each. After 20 minutes the ethanol was removed by aspiration and the plates were refrigerated overnight. Plasmid clones containing *S. diastaticus* glucoamylase genes were identified as colonies that gave a surrounding halo of digestion of the starch azure. Eighteen halo-positive clones were found among 60,000 screened colonies. Halo-positive transformants were picked from the replica plates and plasmid DNA was reisolated by standard methods (Sherman et al., id.).

Figure 2:
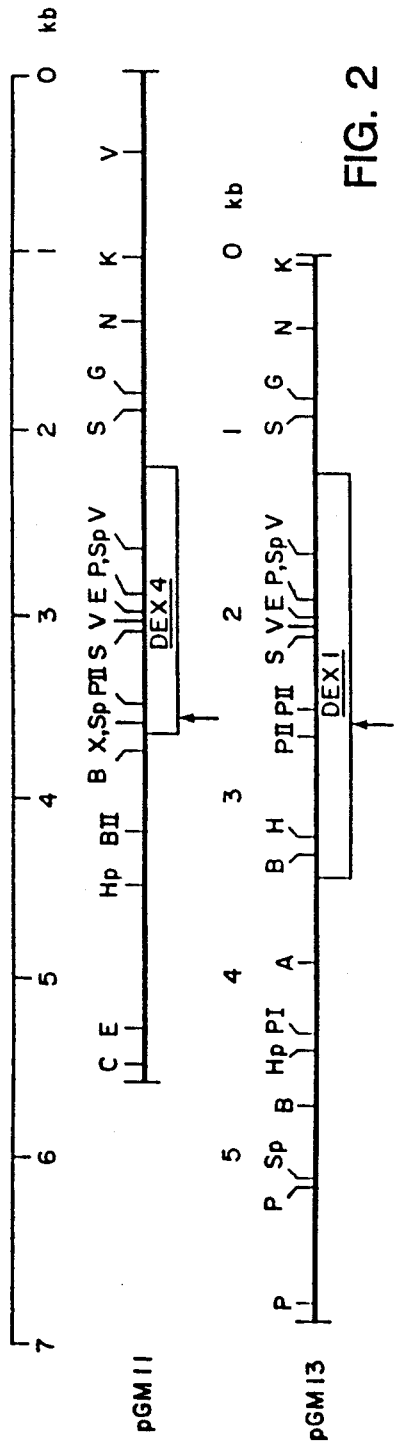

Two plasmids carried the halo-giving phenotype upon retransformation into yeast strain RD61-1D and were chosen for further characterization. We have called these plasmids pGM11 and pGM13. Both pGM11 and pGM13 contained DNA inserts of about 6 kilobases. Restriction maps of the inserts in pGM11 and pGM13 are shown in FIG. 2. As can be seen in the Figure, the restriction maps contain a region of identity and a region where the two inserts are different. Southern blots of *S. cerevisiae* and *S. diastaticus* DNA probed with $^{32}$P-labelled restriction fragments from various portions of pGM11 and pGM13 led to the conclusion that pGM13 contains the *S. diastaticus* DEX1 gene, which encodes a glucoamylase enzyme expressed during vegetative growth, while pGM11 contains a different gene, which we have called DEX4, that exists in both *S. cerevisiae* and *S. diastaticus*. This gene presumably encodes a sporulation-specific glucoamylase which has been previously identified in *S. cerevisiae* (Colonna and Magee (1978) Journal of Bacteriology 134: 844-853).

The fact that colonies containing a multicopy plasmid bearing the DEX4 gene give a halo that is larger than the colony itself on starch azure plates implied that the DEX4 encoded glucoamylase is secreted into the medium. In fact, glucoamylase (GA) activity was found in the supernatant of a liquid culture. To assay secreted GA, cells were grown to saturation in liquid medium consisting of 7 g Difco yeast nitrogen base, 0.7 g uracil drop out mix, 30 g glycerol and 20g ethanol per liter. Cells were removed by centrifugation and 100 μl of supernatant was mixed with 100 μl of 0.1M Na citrate, pH 5.0 containing 10 mg/ml maltotriose (Sigma). The mixture was incubated 1 hour at 30° C. and 25 μl was assayed for glucose with a Yellow Springs Instruments Glucose Analyzer. One unit of GA activity is defined as the amount of enzyme required to produce 10 mg/l glucose under the conditions of the assay described above. This assay showed that the DEX4 gene is poorly expressed during vegetative growth—only 10 units of GA activity were produced from strain RD61-1D carrying this gene on pGM11, which is a multicopy plasmid.

Expression of DEX4 *S. diastaticus* Glucoamylase from Heterologous Promoters The glucoamylase enzyme encoded by the DEX4 gene is potentially of commercial value, and therefore it would be desirable to achieve efficient expression of this enzyme in a yeast strain. To increase expression during vegetative growth, the DEX4 promoter and upstream activation sequence (UAS) were replaced by the equivalent region from the yeast triose phosphate isomerase (TPI) gene. The TPI promoter is carried on plasmid pRY271, as shown in FIG. 1. Plasmid pRY271 carries the replication origins from both pBR322 and the yeast 2 micron circle, so that it and the plasmids described herein derived from pRY271 are shuttle vectors for *E. coli* and *S. cerevisiae*. pRY271 was digested with HindIII, the sticky ends filled in, and ligated with BamHI linkers. The DNA was next digested with BamHI and religated, converting the two HindIII sites of pRY271 into BamHI sites. Two plasmids resulted, pGM24 and pGM25, differing only in the orientation with respect to the plasmid backbone of the BamHI fragment containing the TPI promoter.

Since the first three amino acids of TPI and DEX4 are identical (Met-Ala-Arg), we constructed the fusion junction at the third codon (see FIG. 3, and Alber and Kawasaki (1982) Mol. Appl. Genetics, 1: 419–434), where an EcoRI linker had been inserted in vitro. The DNA sequence between this EcoRI site and the XhoI site of DEX4 was reconstituted with a synthetic 65/69-mer which is shown in FIG. 4. The 2.5 kilobase XhoI-KpnI fragment of the DEX4 gene was removed from pGM11 by digestion with these enzymes, and was purified by gel electrophoresis. Plasmid pGM25 was digested with EcoRI, mung bean nuclease, and KpnI, and the resulting DNA was ligated to the 65/69 bp synthetic linker and the XhoI-KpnI fragment of the DEX4 gene. In the resulting plasmid, pGM30, the DEX4 gene is located downstream from the TPI promoter and upstream activator sequence (i.e. the M to E fragment shown in FIG. 1) and upstream from the TPI terminator sequence (A to B in FIG. 1). When transformed into yeast strain RD61-1D, pGM30 gave about 70 units of GA activity when assayed as described above. A plasmid analogous to pGM30, called pGM29, was constructed in the same way as described above for pGM30, except that the starting plasmid was pGM24, instead of pGM25. The orientation of the DEX4 gene made no difference in expression of DEX4.

The DEX4 glucoamylase gene has also been expressed in *S. cerevisiae* under the control of other transcription-promoting sequences. For example, a DNA fragment including the upstream activator sequences from the *S. cerevisiae* GAL1 gene has been placed upstream from the DEX4 gene, by methods analogous to those described above. A plasmid bearing this construct (pGM19) also directs expression of *S. diastaticus* glucoamylase when transformed into *S. cerevisiae*.

Secretion of Heterologous Proteins Using the DEX4 Signal Sequence pGM30 or pGM29 may be used as a secretion vector for the secretion of any desired heterologous polypeptide, by the insertion of DNA encoding the heterologous polypeptide downstream from the DEX4 signal-encoding sequence. The following examples, utilizing the glucoamylase gene from *A. niger* and the SUC2 gene from *S. cerevisiae*, are illustrative.

Identification of *S. diastaticus* Glucoamylase Signal Sequence

The DNA sequence of DEX4 from the BamHI site to the rightmost SphI site of pGM11 was determined by standard sequencing methods, and is shown in FIG. 3. From base pair +97 onward, the DNA sequence closely matches that of a portion of STA1 (DEX2) (Yamashita et al. (1985) J. Bact. 161: 567–573). However, upstream from base pair +97, the DNA sequence of DEX4 is completely different from that of STA1 (DEX2). Despite this divergence in the 5' end, DEX4 does contain a long open reading frame that begins with an ATG codon and contains a hydrophobic sequence that has all of the properties expected of a secretion signal sequence, including basic amino acids at the 5' end and a favorable signal peptide cleavage site between amino acids alanine$_{24}$ and leucine$_{25}$.

Insertion of *A. niger* Glucoamylase Gene

The gene encoding *A. niger* glucoamylase was obtained as described in Yocum et al., U.S. Ser. No. 736,450, filed May 21, 1985, assigned to the same assignee as the present application, hereby incorporated by reference.

Isolation of the *A. niger* Preglucoamylase Gene

*A. niger* was grown by shaking $10^6$ spores per liter at 30° C. in a medium containing, per liter, 7 g Yeast Nitrogen Base (Difco) and 20 g Soluble Starch (Fisher). Mycelium was harvested by filtration after 3 days of growth and total RNA was prepared by the method of Lucas et al. (1977) J. Bacteriol 130, 1192.

PolyA-containing mRNA was isolated by two passes over olido-dT-cellulose and used to construct a cDNA library by the standard method of G–C tailing into the PstI site of pBR322 (Miniatis et al. (1982) *Molecular Cloning*, Cold Spring Harbor Laboratory Press, Cold Spring Harbor, N.Y.) The cDNA library was transformed into *E. coli* strain YMc9. Single colonies from about 25,000 transformants were screened with a $^{32}$P-labeled synthetic 27 base oligonucleotide probe corresponding to amino acids 259–268 of *A. niger* glucoamylase as published by Svenson el at. (1983) Carlsberg Res. Commun. 48, 529. The sequence of the 27-mer was:

5'-GCATGCGACGACTCCACCTTCCAGCCC-3'

Twelve clones that hybridized with the probe were characterized. One of them, designated p1-19A, contained a 2,200 base pair insert that was shown by DNA sequence analysis to contain the entire coding sequence for preglucoamylase I, as described by Boel et al. (1984) EMBO J. 3, 1097.

Figure 7:
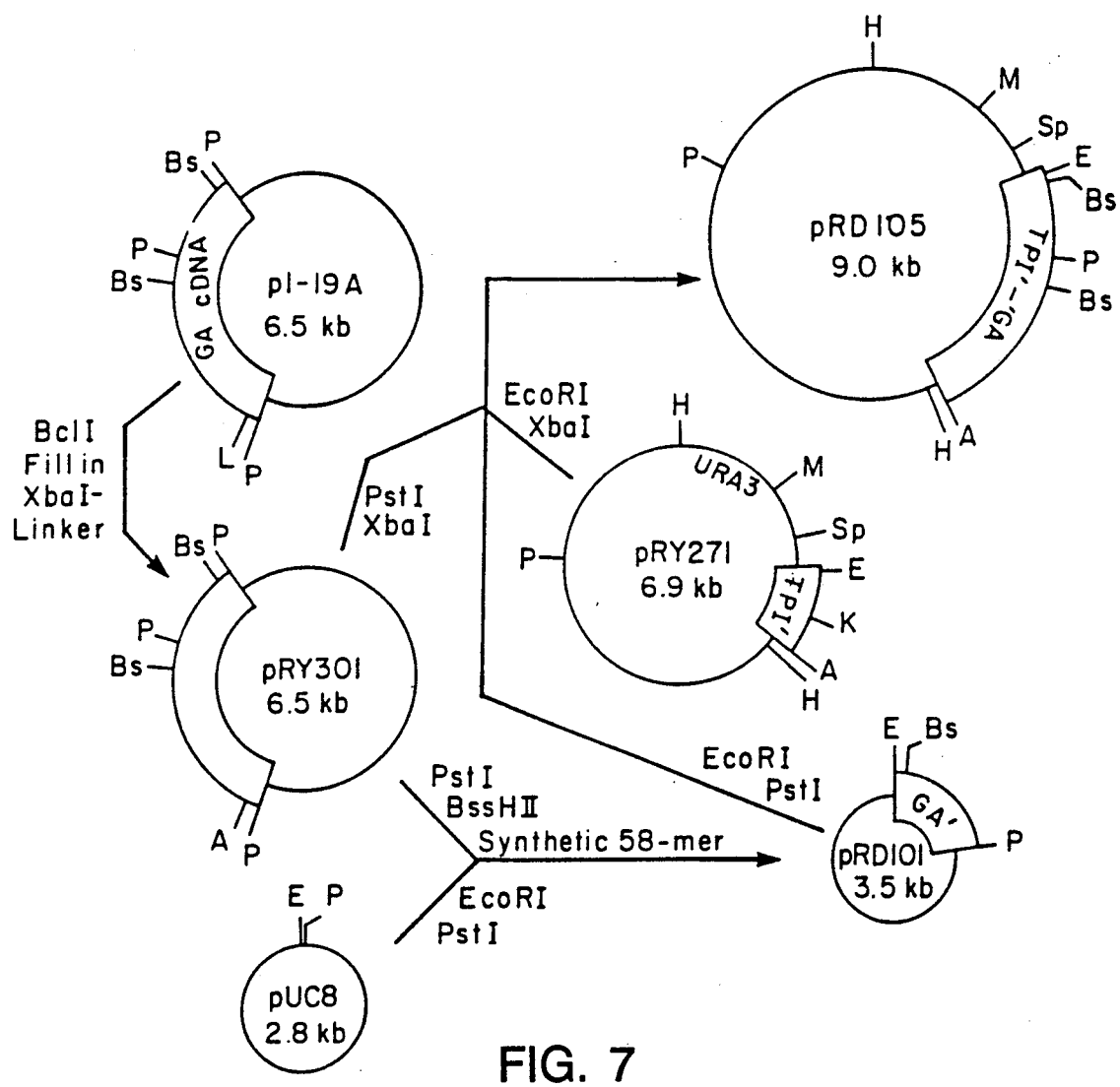
FIG. 7 is a diagrammatic representation of plasmids used in construction of pRD105.

The following constructions and steps are illustrated in FIG. 7.

A unique BclI restriction site was located 54 base pairs downstream from the termination codon of the preglucoamylase I gene in p1-19A. This site was converted into an XbaI site by standard methods (maniatis et al. (1982), id) to yield plasmid pRY301.

A BssHII to PstI fragment containing bases 69–746 of the preglucoamylase I coding sequence was cut out of pRY301 and ligated together with a synthetic 58-mer that replaces sequences lost in the subcloning of the BssHII to PstI fragment (FIG. 8) into the EcoRI to PstI backbone of pUCu8 (New England Biolabs) to give pRD101.

Construction of Glucoamylase Fusion Gene

Preglucoamylase was expressed as a fusion protein from the *S. cerevisiae* TPI promoter. The gene coding for the fusion protein contains DNA including the TPI promoter, the first three amino acids of TPI, an EcoRI linker which creates an isoleucine codon, and preglucoamylase I beginning at the leucine at the sixth position. The DNA sequence around the fusion junction is:

| Met | Ala | Arg | Ile | Leu | Leu . . . |
|-----|-----|-----|-----|-----|-----------|
| ATG | GCT | AGA | ATT | CTA | CTC |
| TAC | CGA | TCT | TAA | GAT | GAG |

The staggered line indicates the EcoRI cleavage site at the fusion junction. The gene fusion was constructed as follows. pRY271 is an expression vector containing an EcoRI linker inserted at codon three of TPI and a natural XbaI site just upstream from the TPI transcription terminator (FIG. 7). Between the aforementioned EcoRI and XbaI sites were inserted two DNA fragments, the EcoRI-PstI piece of preglucoamylase cDNA from pRD101, and the PstI-XbaI piece of preglucoamylase cDNA from pRY301. This yielded pRD105. The glucoamylase gene minus its own signal sequence was isolated from plasmid pRD105 (described in Yocum, id.) by partial digestion with BssHII, followed by digestion with XbaI. A 2.2 kilobase fragment carrying the gene was isolated by gel electrophoresis.

The DEX4 sequences downstream from the XhoI site at base pair +73 were removed by digestion of pGM30 with XhoI and XbaI. This digested plasmid was ligated with the BssHII-XbaI fragment of the *A. niger* glucoamylase gene and with a synthetic 14 base XhoI to BssHII adapter with the sequence indicated in FIG. 4. This gave rise to a plasmid, pRD112, in which the *Aspergillus niger* glucoamylase gene is downstream from the TPI promoter and is downstream from and in-frame with the DEX4 secretion signal-encoding sequence. The *A. niger* GA gene is also upstream from the TPI terminator sequence. The DNA sequence of the 5' end of the gene fusion, including the synthetic sequences, is shown in FIG. 4.

When transformed into yeast strain RD61-1D, pRD112 confers about 100 units of secreted GA activity. The transformant also gives a halo on starch azure plates. Proof that the DEX4 signal sequence was in fact responsible for secretion of the heterologous *A. niger* GA was obtained by substituting glutamic acid for valine at amino acid 17 by in vitro mutagenesis. This disruption of the hydrophobic signal sequence resulted in a dramatic decrease in secreted GA.

Insertion of *S. cerevisiae* SUC2 Gene

Another useful protein capable of being secreted under the control of the DEX4 signal sequence is the enzyme invertase, encoded by the yeast SUC2 gene (Taussig and Carlson (1983) Nuc. Acids Res. 11: 1943–1953; Brown et al. (1984) Mol. Gen. Genet. 197: 351–357). A TPI-DEX4-SUC2 fusion was constructed in two steps as follows. The SUC2 gene is carried on plasmid pAB4 (Brown et al., id), which was obtained from D. Perlman, Brandeis University. An AvaII to XbaI fragment of pAB4 containing bases +90 through +832 of the SUC2 gene (Taussig and Carlson, id) was cloned with a 29/28-mer XhoI-AvaII adapter (see FIG. 6 for sequence) into the XhoI to XbaI backbone of pGM29 to give pGM80. Neither the AvaII to XbaI fragment of SUC2 nor the synthetic adapter contains a signal sequence. The 3' end of the SUC2 gene was then brought in on a 1.3 kilobase XbaI fragment obtained by converting the SalI site downstream from SUC2 in pAB4 (Brown et al., id) to an XbaI site with synthetic XbaI linkers and digesting with XbaI. This step yielded pGM94, which was able to convert a suc⁻ strain, YT455 (α ura3 ade2 suc2 Δ9), to suc⁺ upon transformation. This was evidence that the SUC2 gene is expressed and secreted in these transformed yeast strains. Invertase is ordinarily secreted to the periplasmic space in yeast cells.

Other Heterologous Genes

Any secretable protein can be produced by yeast cells using plasmids derived from pGM29, pGM30 or pRD112. A fragment of DNA encoding the protein to be secreted, not including the region encoding the protein's native signal sequence, can be isolated and inserted into the appropriate DNA backbone of any of these vectors. The DEX4 signal sequence is contained between the EcoRI site destroyed during cloning and the XhoI site of pRD112, so a protein coding sequence not containing its native signal sequence can be inserted at the XhoI site of pRD112. pGM29, pGM30 and pRD112 each supply an ATG translational start codon. These plasmids also supply a transcription terminator between the XbaI and one of the BamHI sites. In many cases insertion of the heterologous gene into these vectors will be facilitated by use of short synthetic adapter DNA fragments, such as the 14 base XhoI to BssHII adapter used in the construction of pRD112 (see FIG. 4).

Deposits

*E. coli* cells transformed with plasmids pRD112 and pGM30 have been deposited in the American Type Culture Collection, Rockville, Md., and given ATCC Accession Nos. 53346 and 53345, respectively. Applicant's assignee, BioTechnica International, Incorporated, acknowledges its responsibility to replace these cultures should they die before the end of the term of a patent issued hereon, and its responsibility to notify the ATCC of the issuance of such a patent, at which time the deposits will be irrevocably made available to the public. Until that time the deposits will be made available to the Commissioner of Patents under the terms of 37 CFR §1.14 and 35 USC §112.

Other Embodiments

The DEX4 signal sequence may be used to direct the secretion of any secretable protein in host yeast cells. The sequence may be used on integrating vectors as well as replicating vectors, and may be used with different transcription promoting sequences and terminator sequences.

It is expected that the DEX1 signal sequence will also be useful in the secretion of heterologous proteins, in ways analogous to those described herein for the DEX4 sequence.

We claim:

1. A vector comprising a DNA sequence encoding a secretory signal sequence of a DEX4 glucoamylase gene from *Saccharomyces diastaticus* or *S. cerevisiae*;

upstream from said signal-encoding sequence, a DNA sequence capable of promoting transcription in yeast, transcription of said signal-encoding sequence being under the control of said transcription-promoting sequence; and downstream from said signal-encoding sequence, a site for the insertion into said vector of a heterologous DNA sequence, encoding a secretable protein in reading frame with said signal-encoding sequence.

2. The vector of claim 1 wherein said heterologous DNA sequence is inserted at said site, transcription of said heterologous DNA sequence being under the control of said transcription-promoting sequence.

3. The vector of claim 1 wherein said DNA sequence capable of promoting transcription comprises the promoter or upstream activation sequence from either the TPI gene or GAL1 gene of *S. cerevisiae*.

4. The vector of claim 2 wherein said heterologous DNA sequence is the glucoamylase gene from *Aspergillus niger*.

5. The vector of claim 4, being pRD112.

6. A yeast cell transformed with the vector of claim 2.

7. A method for producing a desired protein, said method comprising:
 (a) inserting a gene encoding said protein into the vector of claim 1 at said site for insertion;
 (b) said vector into a yeast cell;
 (c) culturing said yeast cell;
 (d) recovering said protein from the growth media.

8. The method of claim 7 wherein said desired protein is glucoamylase from *A. niger*.

9. A vector capable of replication in *S. cerevisiae*, comprising a DEX4 glucoamylase gene derived from *S. diastaticus* or *S. cerevisiae*.

10. The vector of claim 9 wherein said glucoamylase-encoding gene is under the transcriptional control of the promoter derives from the TPI gene of *S. cerevisiae*.

* * * * *